(12) United States Patent
Ye et al.

(10) Patent No.: US 12,268,585 B2
(45) Date of Patent: Apr. 8, 2025

(54) ABSORBENT BODY WITH TOPSHEET COMPOSITE

(71) Applicant: The Procter & Gamble Company, Cincinnati, OH (US)

(72) Inventors: Fengchun Ye, Beijing (CN); Gueltekin Erdem, Beijing (CN); Songmei Zhou, Beijing (CN); Hui Liu, Beijing (CN); Cornelia Sprengard-Eichel, Hofheim am Taunus (DE); Luigi Di Girolamo-Galasso, Schwalbach am Taunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 241 days.

(21) Appl. No.: 17/582,041

(22) Filed: Jan. 24, 2022

(65) Prior Publication Data
US 2022/0249302 A1    Aug. 11, 2022

(51) Int. Cl.
*A61F 13/512*    (2006.01)
*A61F 13/511*    (2006.01)
(Continued)

(52) U.S. Cl.
CPC ...... *A61F 13/512* (2013.01); *A61F 13/51121* (2013.01); *A61F 13/5116* (2013.01);
(Continued)

(58) Field of Classification Search
CPC .......... A61F 13/53708; A61F 13/53747; A61F 13/5116; A61F 13/512; A61F 13/51121; A61F 13/514; A61F 2013/53051
See application file for complete search history.

(56) References Cited

U.S. PATENT DOCUMENTS

| | | | | |
|---|---|---|---|---|
| H1575 H | * | 8/1996 | Daugherty | A61L 15/26 428/137 |
| 2002/0151857 A1 | * | 10/2002 | Bast | A61F 13/495 604/378 |

(Continued)

FOREIGN PATENT DOCUMENTS

| | | |
|---|---|---|
| EP | 3406233 A1 | 11/2018 |
| WO | 2018000410 A1 | 1/2018 |
| WO | WO-2021188330 A1 * 9/2021 ....... A61F 13/15658 |

OTHER PUBLICATIONS

PCT Search Report and Written Opinion for PCT/CN2021/075478 dated Jul. 16, 2021, 14 pages.

*Primary Examiner* — Susan S Su
*Assistant Examiner* — Erin A Kim
(74) *Attorney, Agent, or Firm* — Christian M. Best

(57) ABSTRACT

Disclosed is an absorbent body for an absorbent article, comprising: 1) a first topsheet facing the wearer, the first topsheet being a water permeable nonwoven layer comprising eccentric bicomponent fibers, and having a basis weight of at least about 20 gsm, 2) a second topsheet disposed on the garment facing side of the first topsheet, the second topsheet being a nonwoven layer comprising spunbond fibers and having a positive, at least about 100%, Accumulative One-way Transport Capacity according to the National Standards of the People's Republic of China GB/T 21655.2-2009, wherein the basis weight of the second topsheet is the same or smaller than the basis weight of the first topsheet; 3) an absorbent core disposed on the garment facing side of the second topsheet, and 4) a water impermeable backsheet disposed on the garment facing side of the absorbent core.

18 Claims, 4 Drawing Sheets

(51) Int. Cl.
*A61F 13/514* (2006.01)
*A61F 13/531* (2006.01)
*A61F 13/64* (2006.01)
A61F 13/15 (2006.01)
A61F 13/53 (2006.01)

(52) U.S. Cl.
CPC .......... *A61F 13/514* (2013.01); *A61F 13/531* (2013.01); *A61F 13/64* (2013.01); *A61F 2013/15959* (2013.01); *A61F 2013/530481* (2013.01)

(56) References Cited

U.S. PATENT DOCUMENTS

| | | | |
|---|---|---|---|
| 2014/0343523 A1* | 11/2014 | Viens | D04H 1/498 162/146 |
| 2016/0074237 A1 | 3/2016 | Rosati et al. | |
| 2016/0074243 A1 | 3/2016 | Rosati et al. | |
| 2019/0000690 A1 | 1/2019 | Gizaw et al. | |
| 2020/0093650 A1* | 3/2020 | Denti | A61F 13/51108 |

\* cited by examiner

Schematic diagram of upper and lower sensor probe positions of test sensor

ABSORBENT BODY WITH TOPSHEET COMPOSITE

CROSS REFERENCE TO RELATED APPLICATION

This application claims priority under 35 U.S.C. § 119 to Chinese Patent Application PCT/CN2021/075478, filed on Feb. 5, 2021, the entire disclosure of which is hereby incorporated by reference.

FIELD

This invention relates to absorbent bodies useful for absorbent articles such as diapers having improved fluid handling properties.

BACKGROUND

Absorbent articles for personal hygiene, such as disposable diapers, disposable pants, adult incontinence undergarments, and sanitary napkins, are designed to absorb and contain body exudates, in particular urine, low viscosity fecal matter, and menses (collectively described herein as "fluids"). These absorbent articles may comprise several layers providing different functions, for example, a topsheet, a backsheet, and an absorbent core disposed between the topsheet and the backsheet, among other layers, if desired.

The topsheet is generally liquid permeable and is configured to receive the fluids and aid in directing the fluid towards the absorbent core. In general, topsheets are nonwoven fabrics made of hydrophobic fibers, and made to have higher hydrophilicity via a hydrophilic surfactant treatment applied to the skin-facing surface thereto so that the fluids are attracted to the topsheet and then be channeled into the underlying layers. One of the important qualities of a topsheet is the ability to reduce residency time of the fluids on the topsheet before the fluids are able to be absorbed by the absorbent core. Thus, one criteria of topsheet quality is to reduce the amount of fluid remaining on the topsheet, as well as to reduce the amount of time the fluids spend on the topsheets prior to being absorbed by the absorbent core. If the fluids remain on the surface of the topsheet for too long of a period of time, this may lead to various performance disadvantages. For example, the fluid remaining on the surface of the topsheet may move according to the movement of the wearer and cause leakage. The remaining fluid may cause wet feeling, discomfort, and even skin rash problems to the wearer.

To address the problem of prolonged fluid residency on topsheets, what has been proposed is, for example, providing apertures to allow for faster fluid penetration, and/or providing three-dimensional deformations to reduce contact with the skin, such as those disclosed in PCT publication WO2015/134359A. It has been found, however, that despite the upcharge such processed topsheets may require, the benefit in increasing fluid penetration may not be as significant. Further, in view of the recent desire of the consumer to use products which are environmentally friendly, there is greater pressure to use as little material as possible for absorbent articles. In order to meet such consumer needs, absorbent bodies made of less material and still having good fluid handling properties are desired.

Based on the foregoing, there is a need for an absorbent article having a topsheet with improved fluid handling properties, while maintaining the performance of softness, and wear comfort. There is also a need for an absorbent article which may be economically manufactured.

SUMMARY

The present invention is directed to an absorbent body for an absorbent article having a transversal direction and a longitudinal direction and having a thickness in a vertical direction perpendicular to the transversal direction and longitudinal direction, comprising:
1) a first topsheet facing the wearer, the first topsheet being a water permeable nonwoven layer comprising eccentric bicomponent fibers, and having a basis weight of at least about 20 gsm, or at least about 25 gsm;
2) a second topsheet disposed on the garment facing side of the first topsheet, the second topsheet being a nonwoven layer comprising spunbond fibers and having a positive, at least about 100%, or at least about 400% Accumulative One-way Transport Capacity according to the National Standards of the People's Republic of China GB/T 21655.2—2009, wherein the basis weight of the second topsheet is the same or smaller than the basis weight of the first topsheet;
3) an absorbent core disposed on the garment facing side of the second topsheet, and
4) a water impermeable backsheet disposed on the garment facing side of the absorbent core.

The present invention is also related to absorbent articles comprising such absorbent bodies.

DEFINITIONS

Figure 1:
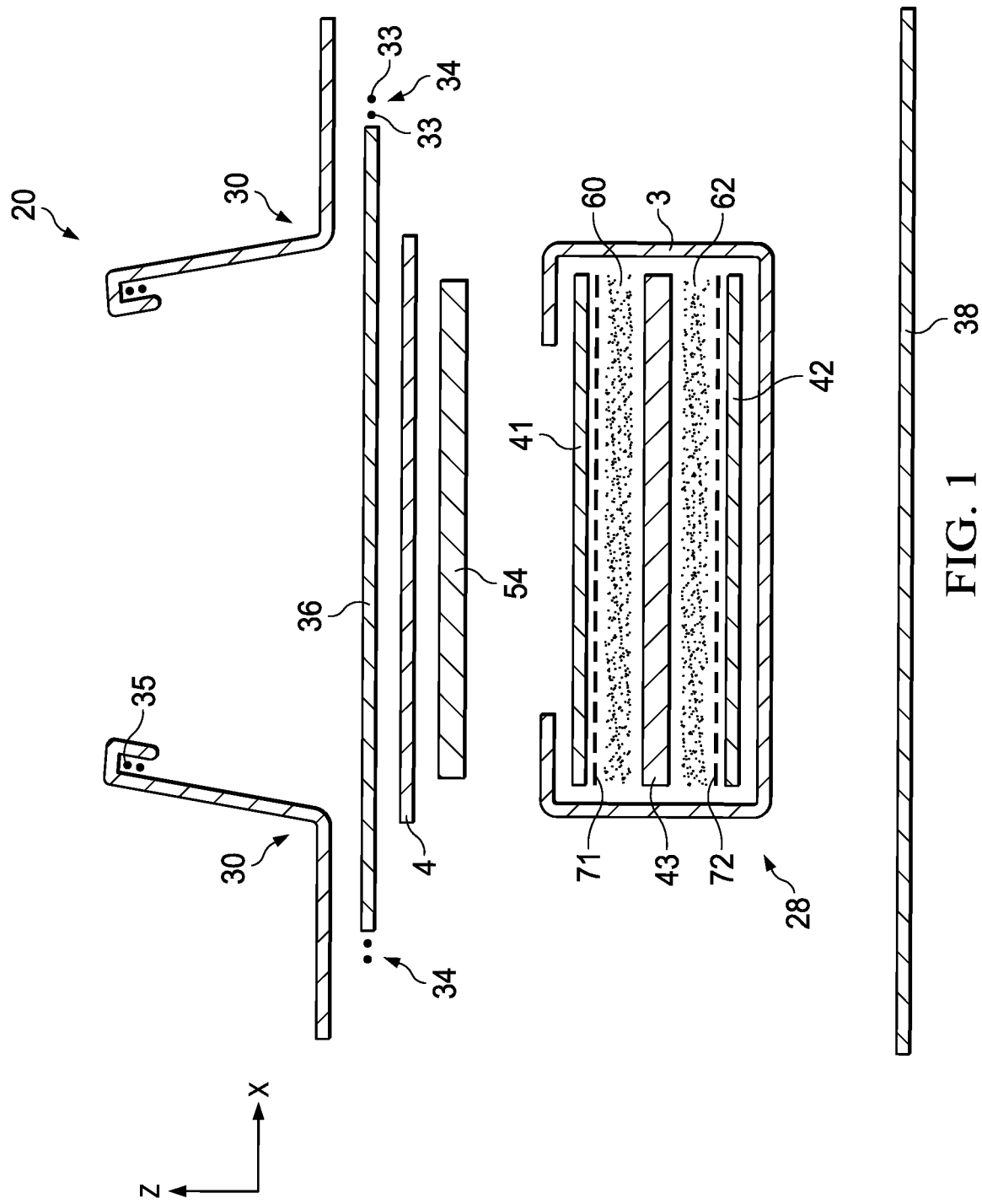
FIG. 1 is a schematic cross section view of an embodiment of the absorbent body of the present invention with the thickness (Z direction) exaggerated.

As used herein, the following terms shall have the meaning specified thereafter: "Absorbent article" refers to articles of wear which may be in the form of taped type diapers, pant type diapers, incontinent briefs, feminine hygiene garments, and the like. The "absorbent article" may be so configured to absorb and contain various exudates such as urine, feces, and menses discharged from the body. The "absorbent article" may refer to a combined merchandise of an outer cover adaptable to be joined with a separable disposable absorbent insert for providing absorbent and containment function, such as those disclosed in PCT publication WO 2011/087503A.

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Proximal" and "distal" refer respectively to the position closer or farther relative to the longitudinal center of the article.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Nonwoven", nonwoven layer" or "nonwoven web" are used interchangeably to mean an engineered fibrous assembly, primarily planar, which has been given a designed level of structural integrity by physical and/or chemical means, excluding weaving, knitting or papermaking (ISO 9092: 2019 definition). The directionally or randomly orientated fibers, are bonded by friction, and/or cohesion and/or adhesion. The fibers may be of natural or synthetic origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter ($g/m^2$ or gsm).

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Hydrophilic" describes surfaces of substrates which are wettable by aqueous fluids (e.g., aqueous body fluids) deposited on these substrates. Hydrophilicity and wettability are typically defined in terms of contact angle and the strike-through time of the fluids, for example through a nonwoven fabric. This is discussed in detail in the American Chemical Society publication entitled "Contact Angle, Wettability and Adhesion", edited by Robert F. Gould (Copyright 1964). A surface of a substrate is said to be wetted by a fluid (i.e., hydrophilic) when either the contact angle between the fluid and the surface is less than 90°, or when the fluid tends to spread spontaneously across the surface of the substrate, both conditions are normally co-existing. Conversely, a substrate is considered to be "hydrophobic" if the contact angle is greater than 90° and the fluid does not spread spontaneously across the surface of the fiber.

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Dimension", "Length", "Width", "Pitch", "Diameter", "Aspect Ratio", "Angle", and "Area" of the article are all measured in a state wherein the article is extended to the Full Stretch Circumference W1 according to the "Whole Article Force Measurement" herein, and utilizing a ruler or a loupe, unless specified otherwise.

"Artwork" refers to a visual presentation to the naked eye, which is provided by printing or otherwise, and having a color. Printing includes various methods and apparatus well known to those skilled in the art such as lithographic, screen printing, flexographic, and gravure ink jet printing techniques.

"Color" or "Colored" as referred to herein includes any primary color except color white, i.e., black, red, blue, violet, orange, yellow, green, and indigo as well as any declination thereof or mixture thereof. The color white is defined as those colors having a L* value of at least 94, an a* value equal to 0±2, and a b* value equal to 0±2 according to the CIE L* a* b* color system.

DETAILED DESCRIPTION

General Description of the Absorbent Body

The present invention is directed to an absorbent body (20) for an absorbent article, the absorbent body (20) comprising a topsheet composite comprising a first topsheet and a second topsheet. FIG. 1 is a schematic cross-sectional view of an exemplary diaper absorbent body (20). Referring to cross section FIG. 1, the absorbent body (20) comprises:
1) a first topsheet (36) facing the wearer, the first topsheet (36) being a water permeable nonwoven layer comprising eccentric bicomponent fibers, and having a basis weight of at least about 20 gsm, or at least about 25 gsm;
2) a second topsheet (4) disposed on the garment facing side of the first topsheet, the second topsheet being a nonwoven layer comprising spunbond fibers and having a positive, or at least about 100%, or at least about 400% Accumulative One-way Transport Capacity according to the National Standards of the People's Republic of China GB/T 21655.2—2009, wherein the basis weight of the second topsheet (4) is the same or smaller than the basis weight of the first top sheet (36);
3) an absorbent core (28) disposed on the garment facing side of the second topsheet (4), and
4) a water impermeable backsheet (38) disposed on the garment facing side of the absorbent core (28).

The components of the absorbent body (20) may be attached directly and indirectly to each other, typically by gluing or heat/pressure bonding. The wearer-facing first topsheet (36) and the backsheet (38) may be attached to each other along their perimeter. Typically, adjacent layers will be joined together using conventional bonding method such as adhesive coating via slot coating or spraying on the whole or part of the surface of the layer, or thermo-bonding, or pressure bonding or combinations thereof. The bonding between components is for clarity and readability not represented in FIG. 1, except for adhesive layers (71, 72). Adjacent layers of the article should be considered to be attached to another unless specifically mentioned otherwise. For example the backsheet and the bottom cover layer of the absorbent core may be typically glued together. The adhesives used may be any standard hotmelt glue as known in the art.

Figure 2:
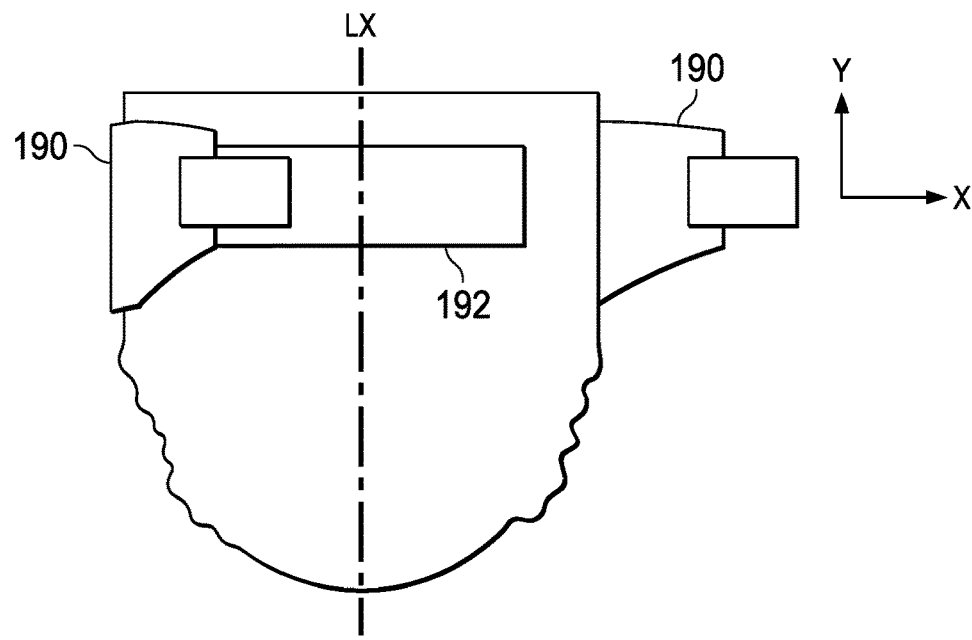
FIG. 2 is a perspective view of an exemplary absorbent article of the taped type.

Referring to FIG. 2, the absorbent article and absorbent body (20) of the present invention have a longitudinal axis LX extending in the longitudinal direction Y of the article, a transverse direction X perpendicular to the longitudinal direction. Referring to FIG. 1, the absorbent article and absorbent body (20) of the present invention have a thickness Z in a vertical direction perpendicular to the transversal direction and longitudinal direction.

First Topsheet

The first topsheet (36) of the present invention forms the wearer facing surface, and is a water permeable nonwoven layer comprising eccentric bicomponent fibers, and having a basis weight of at least about 20 gsm, or more than about 20 gsm, or at least about 25 gsm.

The first topsheet (36) may have a "Median Absorption Pressure" of less than about 6 cm, or less than about 5 cm, according to the measurements herein. Median Absorption Pressure according to the measurements herein is the Capillary Suction Height at which the material has 50% of its Maximum Equilibrium Capillary Sorption Capacity in the absorption phase of the measurement. The Median Absorption Pressure indicates the capillary capacity of the substrate layer. The first topsheet (36) has a high void volume due to the eccentric fibers, thus has a relatively low Median Absorption Pressure.

Without being bound by theory, by having the eccentric microstructure and relatively high basis weight and high void volume, the first topsheet (36) of the present invention provides a cushiony feel while also being compliant, soft-feeling, and non-irritating to the wearer's skin. Further, as further discussed in detail below, when combined with a second topsheet (4), the otherwise retained liquid exudate in the first topsheet (36) is effectively drained into the second topsheet (4) and further quickly transported to the absorbent core (28), such that rewet from the first topsheet (36) is prevented, thus improving dryness on the wear facing side of the first topsheet (36).

The eccentric bicomponent fibers may be selected from the group of core sheath type, side-by-side, and island-in-the-sea type. The eccentric bicomponent fibers may be the core sheath type having high level of crimps. The first topsheet (36) may be made essentially of eccentric bicomponent fibers. A suitable first topsheet (36) may be manufactured from a wide range of materials, such as polyolefin and polyester fibers and filaments, and may be spunbond, carded, wet-laid, meltblown, hydroentangled, or otherwise processed as is known in the art. An exemplary suitable first nonwoven includes airthrough carded nonwoven having a polyester core or a polyolefin core and a polyolefin sheath. Polyester may be polyethylene terephthalate (PET). Polyolefin may be polyethylene (PE) or polypropylene (PP). Natural fibers such as cotton, viscose or silk may be added.

The first topsheet (36) may have openings for enhancing dryness, or for communicating liquid breathability, softness, distribution, or other benefits to the user. Openings of the first topsheet (36) may be apertures having an area of at least about 0.12 mm$^2$ or a smallest dimension of at least about 0.4 mm distributed in aesthetically pleasing shapes and patterns.

The first topsheet (36) may have a plurality of recesses and a plurality of projections, wherein the difference between the recesses and the projections have a Z-direction height in the range of from about 500 μm or more, or from about 500 μm to about 2000 μm. Owing to such structures, fluid may be quickly moved away from the wearer, thereby providing a dry feeling even after insult.

Second Topsheet

The second topsheet (4) of the present invention is disposed on the garment facing side directly beneath the first topsheet (36), the second topsheet (4) being a nonwoven layer comprising spunbond fibers, wherein the basis weight of the second topsheet (4) is the same or smaller than the basis weight of the first topsheet. Further, the second topsheet (4) has a positive, or at least about 100%, or at least about 400% "Accumulative One-way Transport Capacity" according to the National Standards of the People's Republic of China GB/T 21655.2—2009, titled "Textiles—Evaluation of absorption and quick-drying Part 2: Method for moisture management tests". Each of the first topsheet (36) and the second topsheet (4) may have a "Maximum Wetting Radius Immersion Surface" according to the National Standards of the People's Republic of China GB/T 21655.2—2009, wherein the Maximum Wetting Radius Immersion Surface of the second topsheet (4) is smaller than, or smaller than 50% of, or smaller than 30% of, that of the first topsheet (36). The second topsheet (4) may have a Maximum Wetting Radius Immersion Surface of less than about 25 mm, or less than about 10 mm. The difference of Maximum Wetting Radius Immersion Surface between the first topsheet (36) and the second topsheet (4) may be at least about 5 mm, or at least about 10 mm Each of the first topsheet (36) and the second topsheet (4) may have a Median Absorption Pressure according to the measurements herein, wherein the Median Absorption Pressure of the second topsheet (4) is higher than that of the first topsheet (36). The difference of Median Absorption Pressure between the first topsheet (36) and the second topsheet (4) may be at least about 0.5 cmH$_2$O, or at least about 1.0 cmH$_2$O.

"Accumulative One-way Transport Capacity" according to the National Standards of the People's Republic of China GB/T 21655.2—2009 is defined as the difference in the cumulative moisture content between the top and bottom surface of a substrate layer in the unit testing time period, thus indicating how effective moisture may pass through the substrate layer. Without being bound by theory, by having a positive Accumulative One-way Transport Capacity and a basis weight that is the same or smaller than the first topsheet (36), the second topsheet (4) quickly absorbs the liquid exudate captured within the crimped fibers in the first topsheet (36) by capillary effect, and then quickly transports the liquid exudate to the absorbent core (28) for containment. By such effective drainage of liquid exudate into the absorbent core (28), the first topsheet (36) then acts as a barrier between the absorbent core and the wearer, thereby preventing rewetting of the wearer.

"Maximum Wetting Radius Immersion Surface" according to the National Standards of the People's Republic of China GB/T 21655.2—2009 is defined as the maximum wetted ring at the top and bottom surfaces, respectively, where the slopes of water content become greater than tan (15°) for the top and bottom surfaces, respectively. Maximum Wetting Radius Immersion Surface according to the National Standards of the People's Republic of China GB/T 21655.2—2009 indicates how easily the substrate layer may be wetted. "Median Absorption Pressure" according to the measurements herein is the Capillary Suction Height at which the material has 50% of its Maximum Equilibrium Capillary Sorption Capacity in the absorption phase of the measurement. The Median Absorption Pressure indicates the capillary capacity of the substrate layer. Without being bound by theory, by having the Maximum Wetting Radius Immersion Surface of the second topsheet (4) smaller than that of the first topsheet (36), and the Median Absorption Pressure of the second topsheet (4) higher than that of the first topsheet (36), effective drainage of liquid exudate from the first topsheet (36) to the second topsheet (4), and further to the absorbent core (28) is expected.

The composite first and second topsheet of the present invention thus provides the unexpected benefit of providing both improved softness and dryness. The first and second topsheets may be joined by adhesive, embossing, or ultrasonic bonding.

The second topsheet (4) may be hydrophilic, and thus have a contact angle of less than 90°. The second topsheet (4) may be a polyolefin, such as polypropylene (PP), of the SS, SSS, SM, or SMS structure, and having a relatively low basis weight of, for example about 5 gsm to about 20 gsm, or less than about 20 gsm, so long as the basis weight is not greater than that of the first topsheet (36).

Backsheet

The absorbent body (20) of the present invention comprises a water impermeable backsheet (38) disposed on the garment facing side of the absorbent core (28). The backsheet (38) comprises a thin plastic film such as a thermoplastic film having a thickness of less than about 0.10 mm Exemplary backsheet films include those manufactured by Tredegar Corporation, based in Richmond, VA, and sold under the trade name CPC2 film. Other suitable backsheet materials may include breathable materials which permit vapors to escape from the article while still preventing exudates from passing through the backsheet (38). The backsheet (38) may comprise a covering low basis weight nonwoven attached to the external surface of the film to provide for a softer touch.

Absorbent Core

The absorbent body (20) of the present invention comprises an absorbent core (28) disposed on the garment facing side of the second topsheet (4), sandwiched between the second topsheet (4) and the backsheet (38). The absorbent core comprises absorbent material that can absorb and retain body fluid, in particular urine. The absorbent cores (28) according to this invention are typically manufactured in a continuous stream that can be stored and transported for example as a roll of absorbent core material, and are then individualized when integrated in an absorbent article, such as a diaper. Absorbent cores (28) have the most absorbent capacity of the components of the absorbent article and comprises all, or at least the majority of, superabsorbent polymer (herein referred to as "SAP") particles.

The absorbent core (38) of the invention may comprise a high loft material (43) encompassing superabsorbent polymers. The term "high loft" refers to low density bulky fabrics, as compared to flat, paper-like fabrics. High loft webs are characterized by a relatively high porosity. This means that there is a relatively high amount of void space in which superabsorbent polymer particles can be distributed. The high loft material (without the superabsorbent particles) of the invention may have a density at a pressure of 4.14 kPa (0.6 psi) below 0.20 g/cm$^3$, in particular ranging from 0.05 g/cm$^3$ to 0.15 g/cm$^3$. The high loft layer (without the superabsorbent particles) of the invention may have a density at a pressure of 2.07 kPa (0.3 psi) below 0.20 g/cm$^3$, in particular ranging from 0.02 g/cm$^3$ to 0.15 g/cm$^3$. The high loft layer (without the superabsorbent particles) of the invention may have a density at a pressure of 0.83 kPa (0.12 psi) below 0.15 g/cm$^3$, in particular ranging from 0.01 g/cm$^3$ to 0.15 g/cm$^3$. The density can be calculated by dividing the basis weight of the high loft layer by its thickness measured at the respective pressure as described below.

The high loft material (43) may comprise synthetic fibers, optionally mixed with natural fibers such as cellulose or cotton fibers or viscose fibers. The fibers may be made partially or entirely of a relatively resilient synthetic fibers, in particular polypropylene (PP), polyamide (PA, such as nylons) or polyethylene terephthalate (PET) fibers. The diameter of the fibers may for example range from 0.01 mm to 0.50 mm.

The high loft material (43) may in particular have a thickness of from 0.30 mm to 2.00 mm, or from 0.50 mm to 1.5 mm, as measured at a pressure of 4.14 kPa (0.6 psi) and a basis weight of from 15 gsm to 500 gsm.

The high loft material (43) serves as substrate for the SAP particles 60, 62 which are at least partially distributed within its pores. The SAP particles are typically deposited on one side of the high loft material (43) and drawn into the high loft material (43) for example by gravity or a negative pressure on the opposite side of the nonwoven. In this way, some particles remain close to the surface of the high loft material (43) and other, typically smaller, particles may penetrate deeper within the pores of the high loft nonwoven. The SAP particles which are not trapped within the pores of the high loft layer but remain at the surface may be further immobilized by a layer of adhesive (71) or (72). The high loft material (43) may be sandwiched between a top cover layer (41) and a bottom cover layer (42). The top cover layer (41) and the bottom cover layer (42) provide a cover on both sides of the central layer for preventing the SAP particles from falling out of the high loft material (43) during the core and article making process and/or during use of the absorbent article. In addition, the absorbent core may further comprise a wrapping layer (3) that encompasses the high loft material (43) and the two cover layers (41, 42).

Alternatively, the absorbent core may comprise an absorbent layer having superabsorbent polymers disposed between first and second layers of nonwoven material immobilized by a fibrous layer of thermoplastic adhesive material (not shown). The first and second layers of nonwoven materials may be relatively low basis weight nonwoven fibrous webs including synthetic fibers, such as mono-constituent fibers of PE, PET and PP, multiconstituent fibers such as side by side, core/sheath or island in the sea type fibers. Such synthetic fibers may be formed via a spunbonding process or a meltblowing process.

Other Components of the Absorbent Body

The absorbent body (20) may further comprise a liquid management layer 54 directly under the second topsheet (4). The liquid management layer may also be called fluid acquisition or fluid distribution layer. The function of such a layer is to rapidly acquire the fluid from the topsheet away from the wearer-facing side and/or to distribute over a larger area so it is more efficiently absorbed by the absorbent core. It is also possible that such a liquid management layer may be placed between the backsheet and the absorbent core.

Alternatively, the absorbent body (20) may be devoid of any liquid management layer. In other words, the second topsheet (4) may serve as such acquisition or distribution layer that provides an additional wrapping of the absorbent core (28) to avoid SAP particles from escaping outside the core. In that the first and second topsheets offer the function of both quickly transporting liquid exudate to the absorbent core (28) and prevent such transported liquid from returning to the wear-facing surface of the first topsheet (36), a liquid management layer may be omitted. By being devoid of a liquid management layer, the overall thickness of the absorbent body (20) may be kept relatively thin.

Absorbent bodies (20) for diapers may further comprise components that improve the fit of the article around the legs of the wearer, in particular barrier leg cuffs (30) and gasketing cuffs (34). The barrier leg cuffs may be formed by a piece of material, typically a nonwoven, which is partially bonded to the rest of the article and can be partially raised away and thus stand up from the plane defined by the first topsheet (36). The barrier leg cuffs are typically delimited by a proximal edge joined to the rest of the article, typically the topsheet and/or the backsheet, and a free terminal edge intended to contact and form a seal with the wearer's skin. The standing up portion of the cuffs typically comprise an elastic element, for example one or a plurality of elastic strands (35). The barrier leg cuffs provide improved containment of liquids and other body exudates approximately at the junction of the torso and legs of the wearer.

In addition to the barrier leg cuffs, the article may comprise gasketing cuffs (34), which are formed in the same plane as the chassis of the absorbent body (20), in particular which may be at least partially enclosed between the topsheet or the barrier leg cuffs and the backsheet, and may be placed laterally outwardly relative to the upstanding barrier leg cuffs. The gasketing cuffs can provide a better seal around the thighs of the wearer. Usually each gasketing leg cuff will comprise one or more elastic string or elastic element (33) comprised in the chassis of the diaper for example between the topsheet and backsheet in the area of the leg openings.

Application Means

The absorbent body (20) of the present invention may be assembled together with an application means for forming an absorbent article. Referring to FIG. 2, the absorbent article may be the tape type wherein the application means is a fastening system comprising a pair of elongate members (190) and a receiving member (192), the elongate members (190) transversely protruding from the left and right side edges of the back region of the absorbent body (20) and fastenable with the receiving member (192) disposed on the front region. Alternatively, the elongate members (190) may be protruding from the front region and fastenable with the receiving member (192) on the back region. The elongate members (190) may comprise an attaching portion, an extending portion, and refastenable means. The extending portion may be made of highly stretchable laminate for receiving stretching force upon applying the absorbent article, and the refastenable means may be made of material physically engageable with materials of the receiving member (192). The combination of materials useful for the refastenable means and the receiving member (192) include hook and loop, latch and hole, button and hole, hook and hole, low tackifying adhesive agent, and combinations thereof. The receiving member (192) may also have a protruding portion which may or may not be equipped with refastenable means.

Figure 3:
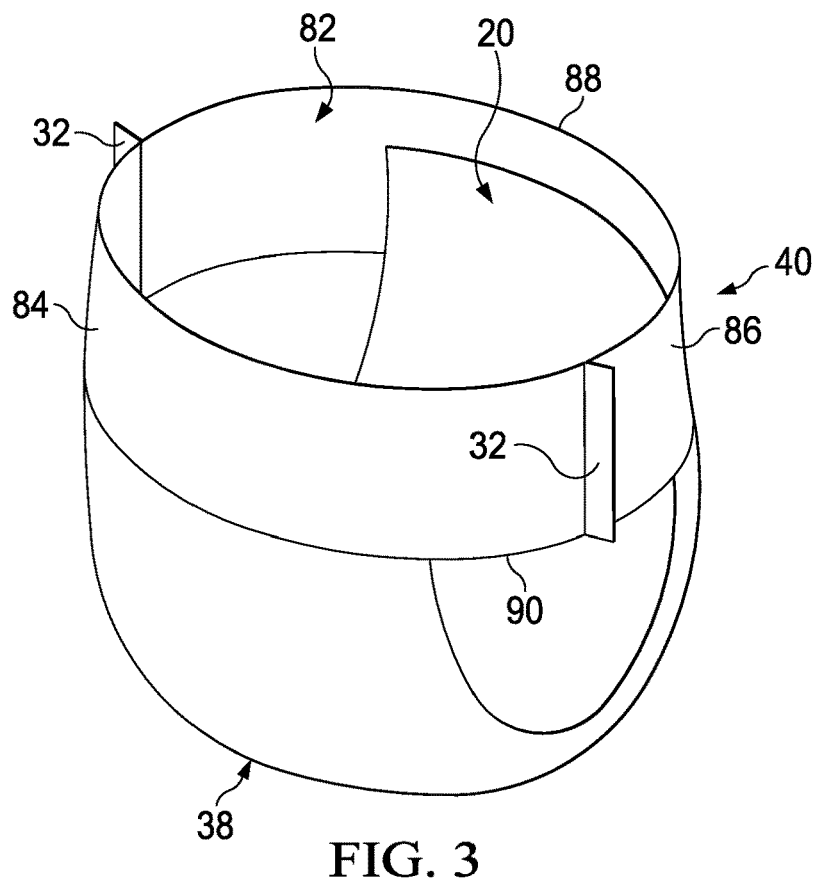
FIG. 3 is a perspective view of an exemplary absorbent article of the pant type.

Referring to FIG. 3, the absorbent article of the present invention may be the pant type wherein the application means is an elastic belt (40) extending transversely from the front and back regions of the absorbent body (20) wherein the center of the front belt (84) is joined to a front waist panel of the absorbent body (20), the center of the back belt (86) is joined to a back waist panel of the absorbent body (20), the front and back belt (84, 86) each having a left side panel (82) and a right side panel (82) where the absorbent body (20) does not overlap, and seamed with each other at the pair of transverse edges as side seams (32) to form a waist opening and two leg openings, each front belt (84) and back belt (86) having transversely continuous proximal and distal edges (90 88), the proximal edge (90) being located closer than the distal edge (88) relative to the longitudinal center of the article. The front and back belt (84, 86) may be formed by an inner sheet, an outer sheet, and a plurality of elastic bodies sandwiched therebetween and running in the transverse direction.

Test Methods

Condition all samples at about 23° C.±2 C.° and about 50%±2% relative humidity for 2 hours prior to testing.

National Standards of the People's Republic of China GB/T 21655.2—2009

Textiles—Evaluation of Absorption and Quick-Drying Properties
Part 2: Method for Moisture Management Tests 1. Scope This part of GB/T 21655 specifies testing and evaluation methods for the moisture management properties in the moisture absorption and quick-drying properties of textiles.
This part is applicable to all kinds of textiles and their products, and can be adopted for other products by reference.

2. Normative References

The clauses in the following documents are hereby incorporated as clauses of this part of GB/T 21655 by reference. For dated references, all subsequent amendments (excluding errata content) or revisions do not apply to this part; however, all parties that have reached an agreement based on this part are encouraged to study whether the latest versions of these documents may be used. For undated references, the latest versions thereof apply to this part.
  GB/T 6529 Textiles-Standard Atmosphere for Conditioning and Testing (GB/T 6529—2008, ISO 139:2005, MOD)
  GB/T 8629—2001 Textiles-Household Washing and Drying Procedures for Testing (eqv ISO 6330:2000)

3. Terms and Definitions

The following terms and definitions apply to this part of GB/T 21655.
3.1 Wetting Time T
  The time it takes for a liquid to come into contact with the surface of a fabric until the fabric starts to absorb moisture. The time required for the fabric to start to absorb the moisture is defined as the time when the slope of the cure of relationship between moisture content and time is greater than or equal to tan 15° for the first time.
3.2 Absorption speed A
  The increase rate of the fabric moisture content per unit time. On the moisture content change curve, it is the average value of the slopes of the moisture content change curve during the test time.
3.3 Maximum Wetting Radius R
  The maximum radius of a wetted area from the time when the fabric starts to wet to the end of a specified time. On the moisture content curve, it is the maximum radius of the wetted area from the first occurrence of the slope of the curve greater than or equal to tan 15° to the end of the test time.
3.4 Spreading Speed of Moisture S
  The cumulative transfer speed of the moisture in the radial direction when spreading to the Maximum Wetting Radius after wetting the fabric surface.

3.5 Accumulative One-Way Transport Capacity O

The capability of the moisture to transfer from an immersion surface of the fabric to a permeation surface. It is expressed as the ratio of the difference in the moisture absorption capacity on both sides of the fabric to the test time.

3.6 Overall Moisture Management Capability M

Characterization of the comprehensive performance of moisture management of the fabric. It is expressed as a weighted value of the moisture absorption rate on the permeation surface of the fabric, the one-way transport capacity, and the moisture spreading speed on the permeation surface.

4. Principle

A fabric sample is placed horizontally. After moisture comes into contact with its immersion surface, the moisture will diffuse along the immersion surface of the fabric, and transfer from the immersion surface of the fabric to a permeation surface, and at the same time diffuse on the permeation surface of the fabric. The change process of the moisture content is a function of time. When a test liquid is dripped on the immersion surface of the sample, a sensor in close contact with the sample is used to measure the moisture management conditions of the moisture, to calculate a series of performance indicators to evaluate the moisture absorption, quick-drying, and moisture-wicking properties of the textile.

5. Equipment and Materials 5.1 Moisture Management Property Tester

Appendix A gives the basic structural principle and requirements of the instrument, and any instrument that can achieve the same effects can be used.

5.2 Materials

Unless otherwise specified, all reagents should be analytically pure, and the water should be grade-3 water.

5.2.1 Test Liquid: 9 g/L Sodium Chloride (NaCl Solution).

6. Standard Atmosphere for Conditioning and Testing 6.1 The standard atmosphere for conditioning and testing shall be a standard atmosphere as specified in GB/T 6529.

6.2 The sample should be conditioned and balanced in a relaxed state before the test. The method and requirements of the conditioning shall be in accordance with the provisions of GB/T 6529. The conditioning should be typically carried out for 16 h or more, synthetic fiber samples at least 2 h, and samples with a nominal moisture regain of zero no conditioning.

7. Sampling and Sample Preparation 7.1 The method and quantity for sample collection shall be determined in accordance with product standards or as agreed upon by parties concerned. For each sample, a full-width fabric of 0.5 m or more is cut, and cloth within 2 m or more from the end should be avoided during sampling; at least one unit is taken for textile products.

7.2 Each sample is cut into two pieces, one of which is used for a pre-washing test and the other for a post-washing test. The sample shall be washed five times according to the GB/T 8629—2001 5A procedure, or according to a method and a number of times agreed upon by parties concerned. The washed sample is dried at a temperature not exceeding 60° C. or under natural conditions.

7.3 Five samples are taken each before and after washing, and the size of the samples is (90±1) mm×(90±1) mm. When the samples are cut, they should be evenly arranged in an area at a distance of 150 mm or more from the edges of the cloth. The samples shall not be located at the same longitudinal and horizontal positions, and defects and wrinkles that affect test results should be avoided. If a product is composed of different fabrics, the sample should be selected from main functional parts.

7.4 Any unevenness of the fabric surface will affect the test results. If necessary, the samples may be ironed by pressing.

8. Test Procedure 8.1.1 Use a clean tweezer to gently grip the corners of a sample to be tested, and place the sample flatly between two sensors of the instrument. Usually with the side close to the body during wearing serving as an immersion surface, the sample is placed in the dripping direction of the test liquid.

8.1.2 Start the instrument, drop 0.2 g±0.01 g of the test liquid on the immersion surface of the fabric within a specified time, and start to record the time and moisture content changes. The test time is 120 s, and the data collection frequency is not less than 10 Hz.

8.1.3 After the test is over, take out the sample, and the instrument automatically calculates and displays the corresponding test results.

8.1.4 Use clean absorbent paper to absorb the excess residual liquid on the sensor plate, and let it stand for at least 1 min. Make sure that there is no residual liquid before another test.

8.1.5 Repeat steps 8.1.1 to 8.1.4 until the five samples have been tested.

9. Result Calculation and Grading 9.1 Calculation 9.1.1 Moisture Absorption Rate A The average moisture absorption rate $A_T$ on the immersion surface and the average moisture absorption rate $A_B$ on the permeation surface are calculated according to formula (1), respectively, and the values are rounded to 0.1.

$$A = \sum_{i=T}^{t_p} \left( \frac{U_i - U_{i-1}}{t_i - t_{i-1}} \right) / (t_p - T) \times f \qquad (1)$$

In the formula,

A—the average moisture absorption rate (divided into the average moisture absorption rate $A_T$ on the immersion surface and the average moisture absorption rate $A_B$ on the permeation surface), in the units of %/s; (if A<0, take A=0);

U—the moisture content of the immersion surface or permeation surface, in the units of %;

T—the wetting time of the immersion surface or permeation surface, in the units of s;

$t_p$—the water inlet time, in the units of s;

$U_i$—the value of the moisture content change curve of the immersion surface or permeation surface at time i;

f—the data sampling frequency.

9.1.2 Moisture Spreading Speed S

The moisture spreading speed S is calculated according to formula (2), and the values are rounded to 0.1.

$$S = \sum_{i=1}^{N} \frac{r_i}{t_i - t_{i-1}} \qquad (2)$$

In the formula,

S—the spreading speed of the moisture (divided into the spreading speed $S_T$ on the immersion surface and the spreading speed $S_B$ on the permeation surface), in the units of mm/s;

$r_i$—the radius of a test ring, in the units of mm;

$t_i$ and $t_{i-1}$—the time taken by the moisture to spread from ring i−1 to ring i;

N—the maximum number of wetted test rings on the immersion surface or permeation surface.

9.1.3 Accumulative One-Way Transport Capacity O

The Accumulative One-way Transport Capacity O is calculated according to formula (3), and the values are rounded to 0.1.

$$O = \frac{\int U_B - \int U_T}{t} \tag{3}$$

In the formula,

O—the Accumulative One-way Transport Capacity;

t—the test time, in the units of s;

$\int U_T$—the moisture absorption capacity of the immersion surface;

$\int U_B$—the moisture absorption capacity of the permeation surface.

9.1.4 Overall Moisture Management Capability M

The overall moisture management capability M is calculated according to formula (4), and the values are rounded to 0.01.

$$M = C_1 A_{BC} + C_2 O_D + C_3 S_{BD} \tag{4}$$

$C_1$, $C_2$, and $C_3$—weight values ($C_1$=0.25, $C_2$=0.5, and $C_3$=0.25).

$A_{BD}$, $O_D$, and $S_{BD}$ are the dimensionless calculated values of the permeation surface moisture absorption rate ($A_B$), the one-way transport capacity (O), and the permeation surface spreading speed ($S_B$), calculated according to formula (5) to formula (7):

$$A_{BD} = \frac{A_B - A_{B,min}}{A_{B,max} - A_{B,min}} \tag{5}$$

$$O_D = \frac{O - O_{min}}{O_{max} - O_{min}} \tag{6}$$

$$S_{BD} = \frac{S_B - S_{B,min}}{S_{B,max} - S_{B,min}} \tag{7}$$

When $A_{BD}$, $O_D$, and $S_{BD} \geq 1$, they are counted as 1; when $A_{BD}$, $O_D$, and $S_{BD} \leq 0$, they are counted as O.

$A_{B,max}$, $A_{B,min}$, $O_{max}$, $O_{min}$, $S_{B,max}$, and $S_{B,min}$ are constants, taking the upper and lower limits of $A_B$, O, and $S_B$ in Table 1, respectively.

9.2 Grading

The grading shall be conducted in accordance with the requirements in Table 1.

TABLE 1

Grading of property indicators

| Property indicator | Grade 1 | Grade 2 | Grade 3 | Grade 4 | Grade 5 |
|---|---|---|---|---|---|
| Immersion time T/s | >120.0 | 20.1-120.0 | 6.1-20.0 | 3.1-6.0 | <3.0 |
| Moisture absorption rate A/(%/s) | 0-10.0 | 10.1-30.0 | 30.1-50.0 | 50.1-100.0 | >100.0 |
| Maximum Wetting Radius R/mm | 0-7.0 | 7.1-12.0 | 12.1-17.0 | 17.1-22.0 | >22.0 |
| Moisture spreading speed S/(mm/s) | 0-1.0 | 1.1-2.0 | 2.1-3.0 | 3.1-4.0 | >4.0 |
| Accumulative One-way Transport Capacity O | <−50.0 | −50.0-100.0 | 100.1-200.0 | 200.1-300.0 | >300.0 |
| Overall moisture management capability M | 0-0.20 | 0.21-0.40 | 0.41-0.60 | 0.61-0.80 | 0.81-1.00 |

Note:

The immersion surface and the permeation surface are graded separately, according to the same grading requirements; grade 5 is the best and grade 1 is the worst.

10. Evaluation of Moisture Absorption and Quick-Drying Properties

If necessary, the corresponding properties of the product can be evaluated according to Table 2. If the corresponding properties of the product before and after washing meet the technical requirements in Table 2, it can be clearly indicated as a product with corresponding properties in the product instructions.

TABLE 2

Technical requirements for moisture absorption
and quick-drying properties of fabrics

| Property | Item | Requirement |
|---|---|---|
| Moisture absorption[a, b] | Wetting time | ≥Grade 3 |
| | Moisture absorption rate | ≥Grade 3 |
| Quick-drying[b] | Maximum Wetting Radius on penetration surface | ≥Grade 3 |
| | Moisture spreading speed on penetration surface | ≥Grade 3 |
| | Accumulative One-way Transport Capacity | ≥Grade 3 |
| Moisture-wicking[b] | Accumulative One-way Transport Capacity | ≥Grade 3 |
| Comprehensive quick-drying | Accumulative One-way Transport Capacity | ≥Grade 3 |
| | Overall moisture management capability | ≥Grade 2 |

[a]Should be met by both the immersion surface and the permeation surface.
[b]Performance requirements can be combined, such as moisture absorption and quick-drying properties, moisture absorption and moisture-wicking properties, etc.

11. Report

The test report should include:
a) the number of this part and the date of the test;
b) the sample description (name, number, raw material, and main specifications, etc.);
c) the washing procedure and number of times;
d) the name and model of the test instrument used;
e) the average and grade of the calculation results in Chapter 9, and the standard deviation shall be reported if necessary;
f) if necessary, the evaluation results of moisture absorption and quick-drying properties shall be reported; and
g) any details deviating from this part and abnormal phenomena in the test.

Appendix A (Informative Appendix) Test Principle and Sensor Structure

Figure 4A:
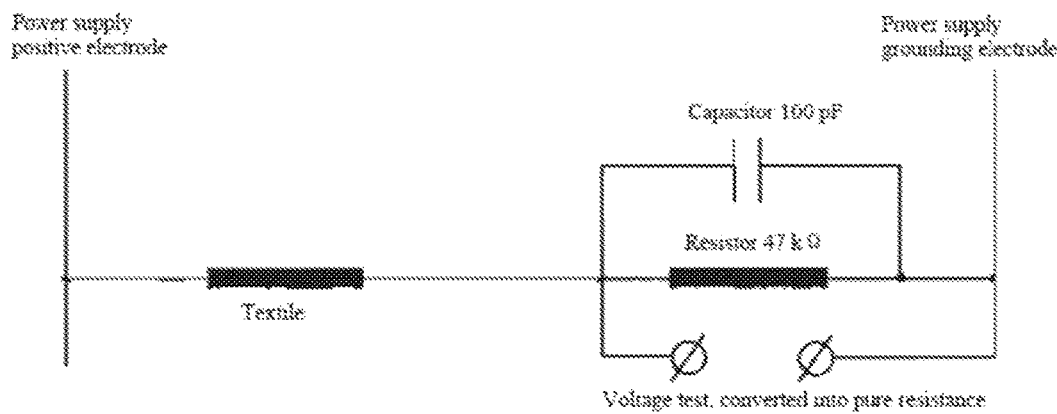
FIGS. 4A-4C are related to the National Standards of the People's Republic of China GB/T 21655.2-2009.
Figure 4B:
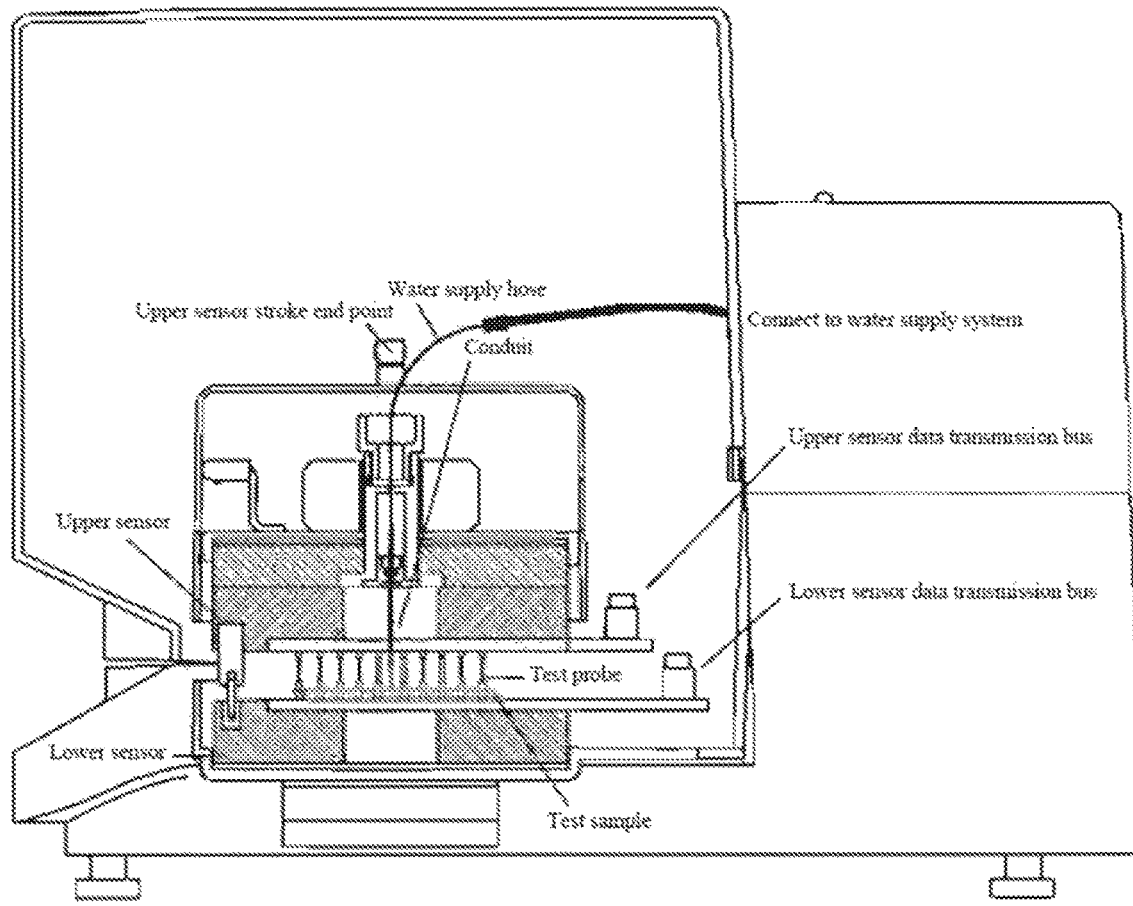
Figure 4C:
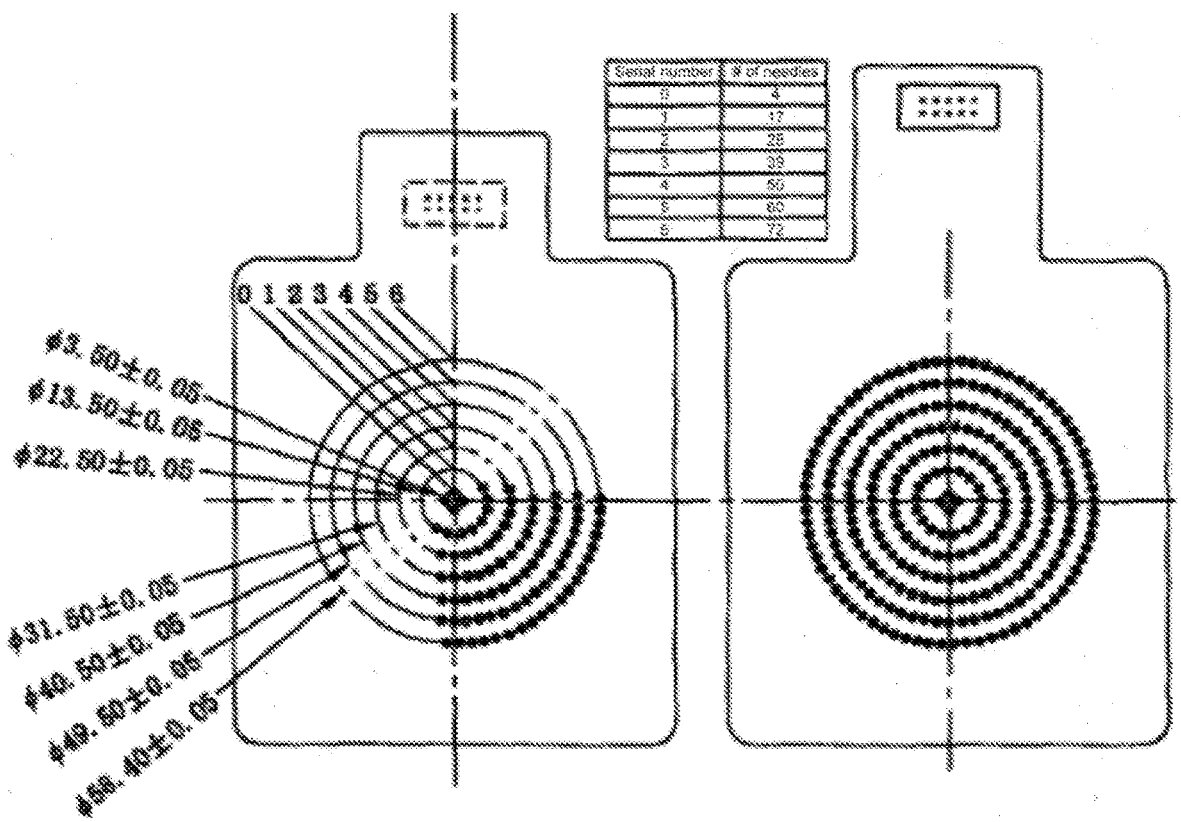

A.1 Test Principle
A.1.1 The principle and structure diagram of the instrument are shown in Figure A.1 (FIG. 4A of this patent application) and Figure A.2 (FIG. 4B of this patent application).
A.1.2 Seven concentric test rings are arranged on upper and lower test sensor planes with a diameter of 58.4 mm, respectively, and the resistance between every two adjacent rings are continuously measured during a solution water spreading test process.
A.1.3 A voltage and a sampling resistance are applied between every two adjacent rings. During the test, since moisture is injected from the center into an immersion surface of a textile, the moisture penetrates and diffuses on the upper and lower sides of the textile. By continuously monitoring the voltage across the sampling resistor, the surface moisture content data of the textile in the ring can be obtained.
A.2 Structure and Composition of Sensor
The test sensor is composed of upper and lower sensor probes/PCB/water supply structure/positioning structure/counterweight parts. The ring size of the upper and lower sensors is the same, as shown in Figure A.3 (FIG. 4C of this patent application).
A.3 Sensor Specifications
A.3.1 Upper Sensor:
consists of spring-connected probes, a total of seven test rings (Figure A.3), ring region distance 5 mm±0.05 mm;
spring probe specifications: contact surface diameter 0.54 mm±0.02 mm, gold-plated copper.
A.3.2 Lower Sensor:
consists of connected probes, a total of seven test rings, ring region distance 5 mm±0.05 mm;
probe specifications: contact surface diameter 1.2 mm±0.02 mm, gold-plated copper; resistance<50 mΩ.
A.4 Test Liquid Delivery System
The technical parameters of the test liquid delivery system are:
delivery time: 20 s;
delivered liquid amount: 0.2 g±0.01 g;
delivered liquid outlet: ring "0" of the upper sensor;
delivered liquid outlet specifications: stainless steel pipe inner diameter 0.5 mm
A.5 Calibration and Adjustment of Instrument
The technical parameters for calibration and adjustment of the instrument are:
standard test solution conductivity: 16 mS±0.1 mS;
delivered test liquid amount: 0.2 g±0.01 g;
water inlet time: 20 s;
test time: 120 s;
test head pressure: 4.65 N±0.05 N (475 gf±5 gf).

Capillary Sorption Test Method

The Capillary Sorption Test Method is used to determine absorption and desorption behaviour of porous materials, and specifically the Median Absorption Pressure. This method makes use of stepped, controlled differential pressure and measurement of associated fluid movement into and out of a porous specimen. The Median Absorption Pressure (MAP) is the differential pressure at which the material has 50% of its Maximum Normalized Capillary Fluid Absorbed (NCFA) in the absorption phase of the measurement and is expressed in $cmH_2O$.

Method Principle

For uniform cylindrical pores, the radius of a pore is related to the differential pressure required to fill or empty the pore by the equation $$\text{Differential pressure} = (2\gamma \cos \Theta)/r;$$

where $\gamma$=liquid surface tension, $\Theta$=contact angle, and $r$=pore radius.

Pores contained in natural and manufactured porous materials are often thought of in terms such as voids, holes or conduits, and these pores are generally not perfectly cylindrical nor all uniform. One can nonetheless use the above equation to relate differential pressure to an effective pore radius, and by monitoring liquid movement into or out of the material as a function of differential pressure characterize the effective pore radius distribution in a porous material. (Because nonuniform pores are approximated as uniform by the use of an effective pore radius, this general methodology may not produce results precisely in agreement with measurements of void dimensions obtained by other methods such as microscopy.)

The Capillary Sorption Test Method uses the above principle and is reduced to practice using the apparatus and approach described in "Liquid Porosimetry: New Methodology and Applications" by B. Miller and I. Tyomkin published in The Journal of Colloid and Interface Science (1994), volume 162, pages 163-170, incorporated herein by reference. This method relies on measuring the increment of liquid volume that enters or leaves a porous material as the differential air pressure is changed between ambient ("lab") air pressure and a slightly elevated air pressure (positive differential pressure) surrounding the specimen in a sample test chamber. The specimen is introduced to the sample chamber dry, and the sample chamber is controlled at a positive differential pressure (relative to the lab) sufficient to prevent fluid uptake into the specimen after the fluid bridge is opened. After opening the fluid bridge, the differential air pressure is decreased in steps to 0, and in this process subpopulations of pores acquire liquid according to their effective pore radius. After reaching a minimal differential pressure at which the mass of fluid within the specimen is at a maximum, differential pressure is increased stepwise again toward the starting pressure, and the liquid is drained from the specimen. It is during the absorption sequence (from maximum differential pressure, or smallest corresponding effective pore radius, to the minimal differential pressure, or largest corresponding effective pore radius), that the fluid absorption by the sample (g/g) at each differential pressure is determined in this method. After correcting for any fluid movement for each particular pressure step measured on the chamber while empty, the fluid absorption by the sample (g/g) for each pressure step is determined via dividing the equilibrium quantity of absorbed liquid (g) associated with this particular step by the dry weight of the sample (g).

Sample Conditioning and Specimen Preparation

The Capillary Sorption Test Method is conducted on samples that have been conditioned in a room at a temperature of 23° C.±2.0° C. and a relative humidity of 50%±5%, all tests are conducted under the same environmental conditions and in such conditioned room. Any damaged product or samples that have defects such as wrinkles, tears, holes, and similar are not tested. Samples conditioned as described herein are considered dry samples for purposes of this invention. Three specimens are measured for any given material being tested, and the results from those three replicates are averaged to give the final reported value. Each of the three replicate specimens has a diameter of 50 mm.

Apparatus

Apparatus suitable for this method is described in: "Liquid Porosimetry: New Methodology and Applications" by B. Miller and I. Tyomkin published in The Journal of Colloid and Interface Science (1994), volume 162, pages 163-170. Further, any pressure control scheme capable of controlling the sample chamber pressure between 0 mmH$_2$O and 1200 mmH$_2$O differential pressure may be used in place of the pressure-control subsystem described in this reference. One example of suitable overall instrumentation and software is the TRI/Autoporosimeter (Textile Research Institute (TRI)/Princeton Inc. of Princeton, N.J., U.S.A.). The TRI/Autoporosimeter is an automated computer-controlled instrument for measuring pore volume distributions in porous materials (e.g., the volumes of different size pores within the range from 1 to 1000 µm effective pore radii). Computer programs such as Automated Instrument Software Releases 2000.1 or 2003.1/2005.1 or 2006.2; or Data Treatment Software Release 2000.1 (available from TRI Princeton Inc.), and spreadsheet programs may be used to capture and analyse the measured data.

Method Procedure

The wetting liquid used is a degassed 0.9% NaCl solution. Liquid density is 1.01 g/cm$^3$, surface tension γ to be 72.3±1 mN/m, and the contact angle cos Θ=0.37. A 90-mm diameter mixed-cellulose-ester filter membrane with a characteristic pore size of 1.2 µm (such Millipore Corporation of Bedford, MA, Catalogue #RAWP09025) is affixed to the porous frit (Monel plates with diameter of 90 mm, 6.4 mm thickness from Mott Corp., Farmington, CT, or equivalent) of the sample chamber.

One skilled in the art knows that it is critical to degas the test fluid as well as the frit/membrane/tubing system such that the system is free from air bubbles. A metal weight weighing 414 g is placed on top of the sample to exert a constant confining pressure of 2.068 kPa during measurement.

The sequence of differential pressures that are run in the test, in mmH$_2$O, is as follows: 800, 400, 380, 360, 340, 320, 300, 280, 265, 250, 235, 220, 205, 190, 175, 160, 145, 130, 115, 100, 90, 80, 70, 60, 55, 50, 45, 40, 35, 30, 25, 20, 15, 10, 5, 0, 5, 10, 15, 20, 25, 30, 35, 40, 45, 50, 55, 60, 70, 80, 90, 100, 115, 130, 145, 160, 175, 190, 205, 220, 235, 250, 265, 280, 300, 320, 340, 360, 380, 400, 800.

The criterion for moving from one pressure step to the next is that fluid uptake/drainage from the specimen is measured to be less than 10 mg/min for 15 s.

A separate "blank" measurement is performed by following this method procedure on an empty sample chamber with no specimen or weight present on the membrane/frit assembly. Any fluid movement observed is recorded (g) at each of the pressure steps. Fluid absorption/retention data for a specimen are corrected for any fluid movement associated with the empty sample chamber by subtracting fluid absorption/retention values of this "blank" measurement from corresponding values in the measurement of the specimen.

Determination of Median Absorption Pressure (MAP)

As described above, for each of the three specimens, the capillary fluid absorbed (g) by each specimen during its absorption cycle is corrected for any effect of the empty chamber and then divided by the dry mass of the specimen to arrive at capillary fluid absorbed normalized by dry sample mass in units of g/g. This is the NFCA. The NCFA is in units of g/g and is calculated for each differential pressure step. The NFCA is a cumulative parameter. For example, the value of NFCA at 300 mmH$_2$O on the uptake portion of the pressure sequence is the total fluid in g/g that has been absorbed between 800 mmH$_2$O and 300 mmH$_2$O and likewise for all other points. The Maximum NCFA for fluid uptake is the value of NCFA at 0 mmH$_2$O.

The Median Absorption Pressure (MAP) is the differential pressure at which the material has 50% of its Maximum NCFA in the fluid uptake portion of the measurement (first half of pressure sequence specified) and is expressed in mmH$_2$O. If the value of NFCA is not exactly 50% for any pressure step in the sequence of pressures, a linear interpolation is made between the two neighboring pressures for which NFCA spans 50% (one above and below) to arrive at MAP for a particular specimen.

The arithmetic mean of three values for MAP for the three specimens is calculated and converted from pressure units of mmH$_2$O to units of cmH$_2$O and is reported as the overall parameter MAP in cmH$_2$O.

Thickness and Density Measurement Method

This method is used to measure the thickness (caliper) of the high loft material (43) in a standardized manner. The density can then be calculated from the thickness and the basis weight of the layer. Unless otherwise mentioned, the thickness and density are indicated for the high loft material in the absence of SAP particles. The measurement should preferably be made on the high loft material before it was converted into an absorbent core and thus free of SAP. If the starting material is not available, the high loft material (43) can be obtained by carefully extracting it from an absorbent core, and removing the majority of SAP particles for example by careful shaking or suction. A freeze spray may be used to separate the central layer from the other layers. The samples should be kept at least 24 hours at 21° C.±2° C. and 50%±10% RH to equilibrate, in particular if they have been previously compressed.

Equipment: Mitutoyo manual caliper gauge with a resolution of 0.01 mm, or equivalent instrument.

Contact Foot: Flat circular foot with a diameter of 16.0 mm (±0.2 mm). A circular weight may be applied to the foot (e.g., a weight with a slot to facilitate application around the instrument shaft) to achieve the target weight. The total weight of foot and added weight (including shaft) is selected to provide the desire pressure, for example 4.14 kPa of pressure (0.6 psi) to the sample. The thickness can be determined at different pressures, using accordingly different weights applied to the foot. The thickness and density measurements indicate the applied pressure, for example measured at 4.14 kPa (0.6 psi) or 1.2 kPa.

The caliper gauge is mounted with the lower surface of the contact foot in a horizontal plane so that the lower surface of the contact foot contacts the center of the flat horizontal upper surface of a base plate approximately 20×25 cm. The gauge is set to read zero with the contact foot resting on the base plate.

Ruler: Calibrated metal ruler graduated in mm
Stopwatch: Accuracy 1 second.
Sample preparation: The central layer is conditioned at least 24 hours as indicated above.
Measurement procedure: The layer is laid flat with the bottom side, i.e. the side intended to be placed towards the backsheet in the finished article facing down. The point of measurement, i.e. the middle of the sample, is carefully drawn on the top side of the layer, taking care not to compress or deform the layer. In the unlikely case that the high loft nonwoven layer is not homogeneous in the transversal direction or longitudinal direction, the values are measured in the center of a sample corresponding to the center of an absorbent core that would be made from the sample.

The contact foot of the caliper gauge is raised and the central layer is placed flat on the base plate of the caliper gauge with the top side of the core up so that when lowered, the center of the foot is on the marked measuring point.

The foot is gently lowered onto the sample and released (ensure calibration to "0" prior to the start of the measurement). The caliper value is read to the nearest 0.01 mm, 10 seconds after the foot is released.

The procedure is repeated for each measuring point. Ten samples are measured in this manner for a given material and the average thickness is calculated and reported with an accuracy of one tenth mm. The basis weight of each sample is calculated by dividing the weight of each sample by their area.

The density, in $g/cm^3$, is calculated by dividing the basis weight (in $g/cm^2$) of the material by the thickness (in cm).

EXAMPLE

Examples 1-3 and Comparative Examples 1-2 having the following first and second topsheet combination as in Table 3 were provided, and some were subject to measurements as described above, and their results are provided in Table 4.

TABLE 3

| Nonwoven Code | Description |
| --- | --- |
| A | 35 gsm eccentric bicomponent carded nonwoven (50% PET core, 50% PE sheath) with Y156 pattern from Yanjan |
| B | 40 gsm eccentric bicomponent carded nonwoven (50% PET core, 50% PE sheath) with Y156 pattern from Yanjan |
| C | 30 gsm concentric bicomponent carded nonwoven (50% PET core, 50% PE sheath) with Y156 pattern from Yanjan |
| D | 10 gsm SS layer spunbond nonwoven (100% PP) from Avgol |
| E | 10 gsm SMS layer spunbond nonwoven (100% PP) from Avgol |
| F | 18 gsm concentric bicomponent carded nonwoven (50% PET core and 50% PE sheath) from Dayuan |
| | Composite first topsheet/second topsheet |
| Example 1 | A/D |
| Example 2 | A/E |
| Example 3 | B/D |
| Comparative Example 1 | B/F |
| Comparative Example 2 | C/F |

TABLE 4

| Nonwoven | Accumulative One-way Transport Capacity (%) | Maximum Wetting Radius Immersion Surface(mm) | Median Absorption Pressure (cmH$_2$O) |
|---|---|---|---|
| A | −111.6 | 28 | 4.6 |
| D | 1018.1 | 2 | 7.6 |
| E | 538.9 | 13 | 10.8 |
| F | −140.3 | 29 | 6.9 |

When formed into an absorbent body, the composite first and second topsheet of Examples 1-3 which meets the parametric requirements of the present invention, provides improved fluid handling properties, while maintaining the performance of softness, and wear comfort.

Example 1, Example 3 and Comparative Example 1 were formed into pant type absorbent articles all having the same structural elements except for the topsheet composite as specified above. The example articles were tested using the Curved Global Acquisition Method and Light Touch Dryness (cGAM-LTD) test, an internal method used to measure the time required to acquire three consecutive 75 ml saline gushes, and the rewet amount of diapers after each gush under low rewet pressure (at 0.03 psi) using an absorbent paper. Lower times cGAM for the different gushes and lower weight for the LTD values are advantageous. The results of the test are summarized in Table 5.

TABLE 5

|  | Example 1 | Example 3 | Comparative Example 1 |
|---|---|---|---|
| cGAM gush1 (s) | 75 | 79 | 78 |
| cGAM gush2 (s) | 265 | 293 | 269 |
| 2nd LTD rewet/g | 0.076 | 0.067 | 0.138 |

Example 1 and Comparative Example 2 were formed into tape type absorbent articles of similar structure, except for the topsheet composite as specified above, and the make up of SAP used in the absorbent core as below.

Example 1: 6.98 g of BASF N7059 and 6.30 g of NS L825

Comparative Example 2: 7.01 g BASF N7059 and 7.01 g of BASF N7059

60 panelists who were caregivers of babies using Size 4 (L size) weighing 9-14 kg with approximately equal number of males and females, and having a mixture of usage experience of major brands of similar price range, were recruited. Each panelist was asked to use 5 test samples at various sequence for 3 days each, and enough samples were provided to test each test sample. Among the 5 test samples were Example 1, and Comparative Example 2. The panelists were asked to report the number of incidents of leakage of urine and fecal matter. The percentage of leakage is provided in Table 6.

TABLE 6

| Value | Example 1 | Comparative Example 2 |
|---|---|---|
| Number of urine change samples | 1011 | 997 |
| Percentage of urine leakage (%) | 0.3% | 0.8% |
| Number of fecal matter change samples | 283 | 270 |
| Percentage of fecal matter leakage (%) | 0.0% | 1.1% |

Compared to Comparative Example 2, Example 1 provided statistically significantly less percentage, at 95% confidence level, of both urine and fecal matter leakage, despite having less amount of SAP in the absorbent core.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" Further, every numerical range given throughout this specification includes every narrower numerical range that falls within such broader numerical range.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent body for an absorbent article having a transversal direction and a longitudinal direction and having a thickness in a vertical direction perpendicular to the transversal direction and longitudinal direction, comprising:
    a first topsheet facing the wearer, the first topsheet being a water permeable nonwoven layer comprising eccentric bicomponent fibers, and having a basis weight of at least about 20 gsm, wherein the first topsheet comprises apertures having an area of at least 0.12 mm$^2$;
    a second topsheet disposed on the garment facing side of the first topsheet, the second topsheet being a nonwoven layer comprising spunbond fibers and having a positive, at least about 100%, Accumulative One-way Transport Capacity, according to the National Standards of the People's Republic of China GB/T 21655.2—2009, wherein a basis weight of the second topsheet is the same as or smaller than the basis weight of the first topsheet;
    an absorbent core disposed on the garment facing side of the second topsheet; and
    a water impermeable backsheet disposed on the garment facing side of the absorbent core;
    wherein the absorbent core comprises a high loft material encompassing superabsorbent polymers.

2. The absorbent body of claim 1, wherein each of the first topsheet and the second topsheet have a Maximum Wetting Radius Immersion Surface, according to the National Standards of the People's Republic of China GB/T 21655.2—2009, and wherein the Maximum Wetting Radius Immersion Surface of the second topsheet is smaller than 50% of that of the first topsheet.

3. The absorbent body of claim 2, wherein the second topsheet has a Maximum Wetting Radius Immersion Surface, according to the National Standards of the People's Republic of China GB/T 21655.2—2009 of less than about 25 mm.

4. The absorbent body of claim 1, wherein each of the first topsheet and the second topsheet have a Median Absorption Pressure, according to the Capillary Sorption Test Method herein, and wherein the Median Absorption Pressure of the second topsheet is higher than that of the first topsheet.

5. The absorbent body of claim 4, wherein the first topsheet has a Median Absorption Pressure of less than about 6 cmH$_2$O, according to the measurements herein.

6. The absorbent body of claim 1, wherein the bicomponent fiber for making the first topsheet is selected from the group of core sheath type, side-by-side, and island-in-the-sea type.

7. The absorbent body of claim 6, wherein the first topsheet is an airthrough carded nonwoven having a polyester core or a polyolefin core, and a polyolefin sheath.

8. The absorbent body of claim 1, wherein the second topsheet has a contact angle of less than 90°.

9. The absorbent body of claim 1, wherein the absorbent body is devoid of a liquid management layer.

10. The absorbent body of claim 1, wherein the absorbent core comprises an absorbent layer having superabsorbent polymers disposed between first and second layers of nonwoven material immobilized by a fibrous layer of thermoplastic adhesive material.

11. An absorbent article comprising the absorbent body of claim 1, and an application means, wherein the application means is selected from the group of a fastening means and an elastic belt.

12. An absorbent body for an absorbent article having a transversal direction and a longitudinal direction and having a thickness in a vertical direction perpendicular to the transversal direction and longitudinal direction, comprising:
    a first topsheet facing the wearer, the first topsheet being a water permeable nonwoven layer comprising eccentric bicomponent fibers, and having a basis weight of more than 20 gsm, wherein the first topsheet comprises apertures having a smallest dimension of at least 0.4 mm;
    a second topsheet disposed on the garment facing side of the first topsheet, the second topsheet being a nonwoven layer comprising spunbond fibers and having a basis weight of less than 20 gsm;
    an absorbent core disposed on the garment facing side of the second topsheet; and
    a water impermeable backsheet disposed on the garment facing side of the absorbent core;
    wherein the absorbent core comprises a high loft material encompassing superabsorbent polymers.

13. The absorbent body of claim 12, wherein the bicomponent fiber for making the first topsheet is selected from the group of core sheath type, side-by-side, and island-in-the-sea type.

14. The absorbent body of claim 13, wherein the first topsheet is an airthrough carded nonwoven having a polyester core or a polyolefin core, and a polyolefin sheath.

15. The absorbent body of claim 12, wherein the absorbent body is devoid of a liquid management layer.

16. The absorbent body of claim 12, wherein the absorbent core comprises an absorbent layer having superabsorbent polymers disposed between first and second layers of nonwoven material immobilized by a fibrous layer of thermoplastic adhesive material.

17. The absorbent body of claim 12, wherein the first topsheet is apertured.

18. An absorbent article comprising the absorbent body of claim 12, and an application means, wherein the application means is selected from the group of a fastening means and an elastic belt.

\* \* \* \* \*